United States Patent [19]  [11]  4,379,164
Tömösközi et al.  [45]  Apr. 5, 1983

[54] VASODILATIVE 4-THIA-PGI$_1$ AND 4-SULFINYL-PGI$_1$ AND DERIVATIVES THEREOF

[75] Inventors: István Tömösközi; Péter Györy; Gabor Kovacs; Sandor Virag; Peter Körmöczy; István Stadler, all of Budapest, Hungary

[73] Assignee: Chinoin Gyogyszer es Vegyeszeti Termekek Gyara R.T., Budapest, Hungary

[21] Appl. No.: 314,433

[22] Filed: Oct. 23, 1981

[30] Foreign Application Priority Data

Oct. 28, 1980 [HU] Hungary ................................. 2596

[51] Int. Cl.$^3$ ................. A61K 31/335; C07D 307/935
[52] U.S. Cl. ..................................... 424/285; 542/426; 549/465
[58] Field of Search ................... 260/346.22; 542/426; 424/285; 549/465

[56] References Cited
U.S. PATENT DOCUMENTS
4,125,713 11/1978 Nelson ............................ 260/346.22

Primary Examiner—Henry R. Jiles
Assistant Examiner—Bernard Dentz
Attorney, Agent, or Firm—Karl F. Ross; Herbert Dubno

[57] ABSTRACT

A compound having vasodilative, bronchodilative, stomach-mucosa-protective and platelet-aggregation-inhibiting activity has the formula A 4-thia- or 4-sulfinyl-PGI$_1$-compound of the formula I

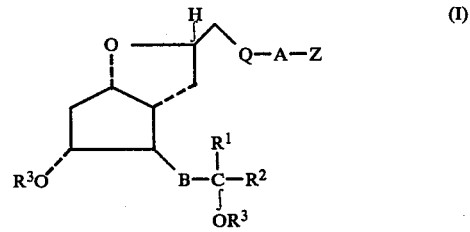

wherein
Q stands for —S— or —SO—,
A stands for $C_{1-6}$ straight or branched chain alkylene,
B stands for ethylene, vinylene or ethinylene,
$R^1$ represents hydrogen or $C_{1-4}$ alkyl,
$R^2$ represents $C_{1-8}$ straight or branched chain alkyl or mono-substituted aryl-oxy-methyl,
$R^3$ stands for hydrogen or acetyl, and
Z represents —COOH, —CN, —CH$_2$OH or —COOW, wherein W stands for an equivalent of a pharmacologically acceptable cation or $C_{1-4}$ alkyl.

8 Claims, No Drawings

VASODILATIVE 4-THIA-PGI₁ AND 4-SULFINYL-PGI₁ AND DERIVATIVES THEREOF

FIELD OF THE INVENTION

The present invention relates to novel biologically active compounds of the formula I

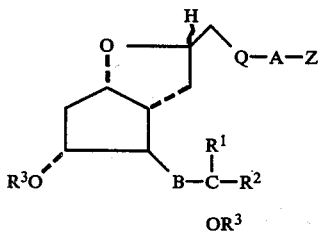

and pharmaceutical compositions containing same. The invention also relates to a process for the preparation of the compounds and of the compositions.

In the formula I
Q stands for —S— or —SO—
A stands for straight or branched chain alkylene containing 1 to 6 carbon atoms,
B represents ethylene, vinylene or ethynylene,
$R^1$ stands for hydrogen or alkyl having 1 to 4 carbon atoms,
$R^2$ stands for straight or branched chain alkyl having 1 to 8 carbon atoms or if desired mono-substituted aryloxy-methyl,
$R^3$ represents hydrogen or acetyl,
Z stands for —COOH, —CN, —CH₂OH or —COOW, wherein W stands for an equivalent of a pharmacologically acceptable cation or alkyl having 1 to 4 carbon atoms.

In the formula I the steric configuration of the hydrogen atom on the 3-carbon atom of the 2-oxabicyclo[3.3.0]octane structure may be α- or β- (exo or endo). Both epimeric series belong to the invention. Similarly the steric configuration of the hydroxyl group of side chain substituent on the 6-carbon atom of the structure may be S— or R—.

The compounds according to the invention include racemates or optically active enantiomers.

BACKGROUND OF THE INVENTION

The significant representative of the endogenic prostaglandins discovered in 1976 i.e. prostacycline (PGI₂) shows a considerable biological activity (Prostacyclin, ed.: J. R. Vane and S. Bergström Raven Press, N.Y. 1979).

From a therapeutical point of view the blood aggregation inihibiting, the peripheric vasodilative and cytoprotective activity of the prostacycline are of particular importance. The extraordinary instability of prostacycline creates a limit to the therapeutic applicability of these useful biological properties. Its half life in aqueous solutions at neutral pH is only 3.5 minutes. More useful than prostacycline are those therapeutically active substances which are much more stable than prostacycline and preserve biological activity.

DESCRIPTION OF THE INVENTION

We have found that compounds of the formula I meet the above criteria. Compounds of formula I inhibit the thrombocyte aggregation at a very low concentration, possess excellent vasodilative (hypotensive) activity and, bronchodilative effect and protect the mucosa of the stomach. The compounds of the formula I also have a much higher stability than prostacycline. The compounds are stable in a wide range of pH from a thermic and hydrolytic point of view as well.

The compounds of the formula I show a further advantage, i.e. depending on their structure some representatives of the compounds show in the mentioned fields of activity a higher selectivity than prostacycline.

The inhibition of thrombocyte aggregation induced by ADP or collagen was investigated according to Born. The active ingredient concentration is given hereinbelow which inhibited the aggregation of the human plasma rich in thrombocytes (PRP) in 50%.

| | Aggregation inducing agent | |
|---|---|---|
| | ADP | Collagen |
| 4-thia-PGI₁(Na—salt) | 200 ng/ml | µg/ml |
| 4-thia-PGI₁—methyl-ester | 2.5 µg/ml. | 25 µg/ml.; |
| 4-thia-PGI₂—methyl ester | 2.5 µg/ml. | 25 µg./ml. |

The haemodynamic activity of the active ingredients was investigated in cats. The results show that 4-thia-PGI₁ effected the circulation at a dose of 100 µg/kg. whereas the same effect can be achieved with a dose of 1 µg./kg. of PGI₂. This indicates the significant reduction of the undesired side-effects.

4-thia-PGI₁ relaxes the guinea-pig trachea. This relaxation cannot be inhibited by Inderal [1-isopropylamino-3-(1-naphthyl-oxy)-propan-2-ol]. The extent of relaxation was as follows:
a dosage of 1 µg./ml. of 4-thia-PGI₁:50%
a dosage of 10 µg./ml. of 4-thia-PGI₁:83%.

The compounds of the formula I may be employed as active ingredients of pharmaceutical compositions. When preparing the pharmaceutical compositions the conventionally used filling agents, diluents, flavoring agents, aroma substances, additives facilitating formulation, adjusting osmotic pressure and pH, stabilizers and agents promoting absorption may be added to the active ingredient. The compositions may be prepared in liquid, semi-liquid or solid form. The solid compositions may be prepared e.g. in the form of tablets, capsules, dragees, pills or powders etc., the liquid compositions in the form of infusion, inhalant and injectable solutions, compress liquids, fluid medicines, drops etc. and the semi-liquid compositions in the form of cremes, ointments, balsams, suppositories etc. The solutions and emulsions may be, of course, processed by using known carrier gases and spray products are obtained.

The necessary dosage of the active ingredients depends on severity of the disorder or disease to be treated, on the rate of resorption of the medicine, on the sensitivity of the patient or the organ to be treated. The dosage and the preferred route of administration may be determined by the physician. It is desirable to employ such doses, which are suitable to achieve the desired therapeutical effect, but do not cause side effects or only to a negligible extent. The used dosage is generally in the range from 1 µg./kg. to 100 mg./kg.

The compounds of the formula I are prepared from compounds of the formula II

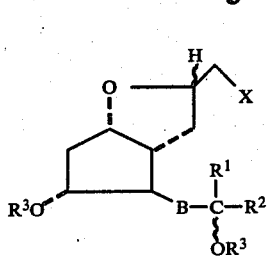

(II)

In formula II B, $R^1$ and $R^2$ are as defined above and X represents bromine, iodine, $R^3$ stands for hydrogen or acetyl.

Compounds of the formula II are known compounds (Tetrahedron Lett., 1978, 581.).

Compounds of the formula I may be prepared according to the invention from compounds of the formula II by (a) replacing the halogen atom of the halo-derivatives of the formula II—wherein X stands for bromine or iodine—by an (—SH) group by reacting it with thiourea, alkali metal sulfides, alkali metal hydrogen sulfides, hydrogen sulfide, or a mercapto acetic acid salt and treating it with acid, and reacting the obtained thiols of the formula III

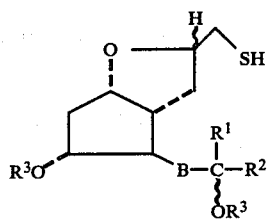

(III)

after adding bases with ethylene derivatives of the formula V

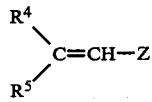

(V)

wherein $R^4$ and $R^5$ stand independently on each other for hydrogen or $C_{1-3}$ alkyl, or alkyl halides of the formula VI

X—A—Z    (VI)

wherein A, Z and X are as given above, or (b) reacting halogen derivatives of the formula II with salts of mercapto carboxylic acids of the formula VII

HS—A—COOH    (VII)

in order to prepare compounds of the formula I wherein Z stands for carboxyl, and oxidizing if desired, compounds of the formula I obtained by process variant (a) or (b) containing —S— in place of Q to compounds of the formula I containing —SO— in place of Q and/or converting the obtained compounds to another compound of the formula I by esterification, salt formation, amidation, hydrolysis, reduction.

According to process variant (a) compounds of the formula II are preferably treated with thiourea, or an alkali metal sulfide, alkali metal hydrogen sulfide, or hydrogen sulfide in $C_{1-4}$ alcohols or aqueous mixtures thereof at 25°–120° C. and the obtained product is converted to compound of the formula III by alkaline hydrolysis and reacidification or acid treatment.

It is particularly preferred to react the compounds of the formula II with a salt of mercapto acetic acid, preferably with sodium mercapto acetate, whereby compounds of the formula IV

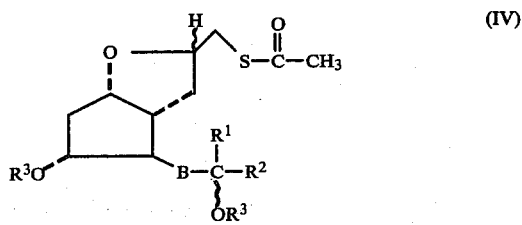

(IV)

are obtained which after alkaline hydrolysis result in compounds of the formula III.

The obtained compounds of the formula III are reacted with ethylene derivatives of the formula V in the presence of a catalytic amount of alkali metal hydroxides or alkali metal alkoxides, preferably sodium ethoxide or tertiary amines, preferably triethyl amine or pyridine in $C_{1-4}$ alkanol or aqueous alkanol solution or they are reacted in the presence of an equivalent or an excess basis with alkyl halides of the formula VI in $C_{1-4}$ alkanol or preferably in acetone.

Process variant (b) is preferably conducted in $C_{1-4}$ alkanols, such as ethanol or in a mixture of said alkanols and water at 25° to 70° C.

The salts of mercapto-carboxylic acids of the formula VII are ambident nucleophilic agents, but the reaction of the "soft" thiolate ion on the similarly "soft" carbon atom bearing electrophilic halogen is much more "preferential" than that of the "hard" nucleophilic type carboxylate ion, thus only compounds of the formula I are obtained. (The above reaction is disclosed in detail in J. Chem. Educ., 1968, 45., 581. and 683.).

Compounds of the formula I which contain —S in the place of Q may be converted to compounds of the formula I containing —SO— in the place of Q in known solvents, preferably in chlorinated hydrocarbons, such as dichloromethane, by oxidizing same with organic peracids such m-chloro-perbenzoic acid or per-acetic acid.

The additional conversion of the compounds of the formula I such as esterification, salt formation, amidation, hydrolysis and reduction may be performed by methods known per se. For example the ester groups may be converted to compounds bearing free carboxylic groups or carboxylic groups converted to salts and bearing free hydroxyl groups (alcohols). The free carboxyl groups may be esterified and amidated by methods known per se. The amides may be dehydrated to result in nitriles whereas when hydrolyzed nitriles or amides give free acids.

The further details of the invention are illustrated by the following Examples which serve merely for illustration and not for limitation.

EXAMPLE 1

3β-(Acetyl-mercapto-methyl)-6β-(3α-acetoxy-oct-1-trans-enyl)-7α-acetoxy-cis-2-oxabicyklo[3,3,0]octane (Compound of the formula IV wherein $R^3$=acetyl, B=trans-vinylene, $R^1$=hydrogen, $R^2$=n-pentyl)

0.956 g. (0.002 mole) of 3β-iodo-methyl-6β-(3α-acetoxy-oct-1-trans-enyl)-7α-acetoxy-cis-2-oxabicyclo(3.3.0)octane (formula II wherein X=iodine, B, $R^1$, $R^2$, $R^3$ are as given above) are dissolved in 10 ml. anhydrous acetone and under steady stirring 0.21 g. (0.204 mole) of sodium mercapto acetate is added. The reaction mixture is heated under stirring in a 60° C. bath. The reaction is monitored by thin layer chromatography. $R_f$ of the starting material=0.53 and $R_f$ of the product=0.47 eluted with an 1:1 mixture of hexane-ethyl acetate on silicagel. When the starting material is consumed the reaction mixture is poured on 40 ml. of water of a temperature of 0° C., extracted with 3×50 ml. of ether and the ether solution is washed with 2×20 ml. cold water, and 20 ml. saturated sodium chloride solution, dried above magnesium sulphate and evaporated. The named compound is obtained in the form of a thick oil in an amount of 0.8–0.85 g. (94–99%) which is suitable for further operations but can be chromatographed on silicagel, as eluant a 1:2 mixture of ethyl acetate and hexane is used.

$R_f$=0.26 (ethyl acetate-hexane=1:2).

$H^1$-NMR (CDCl$_3$): 5.48 (m, 2H), 5.18 (m, 1H), 4.75 (q, 1H), 4.48 (m, 1H), 4.15 (m, 1H), 3.09 (dd, 2H), 2.34 (s, 3H), 203 (s, 3H), 2.00 (s, 3H), 0.87 (t, 3H) ppm.

EXAMPLE 2

3β-(Mercapto-methyl)-6β-(3α-hydroxy-oct-1-trans-enyl)-7α-hydroxy-cis-2-oxabicyclo[3.3.0]octane (Compound of the formula III wherein $R^1$=$R^3$=hydrogen, B=trans-vinyl, $R^2$=n-pentyl)

1.472 g. of 3β-iodo-methyl-6β-(3α-hydroxy-oct-1-trans-enyl)-7α-hydroxy-cis-2-oxabicyclo[3.3.0]octane are dissolved in 5 ml. of anhydrous ethanol, 0.3 g. of thiourea is added to the solution and the mixture is heated under reflux until the starting material is consumed. The reaction is terminated within 60–80 hours. The $R_f$ value of the iodo-compound of the formula II is 0.38 (eluent: an 1:1 mixture of hexane-acetone), the formed thiuronium salt substantially remains at the starting point. When the reaction is completed ethanol is removed by rotating evaporator, the residue is dissolved in 5 ml. of 1 M aqueous sodium hydroxide solution and the mixture is stirred at 80° C. After cooling the reaction mixture is diluted with 10 ml. of water, acidified with 2 ml. of 1 M aqueous sodium hydrogen sulphate solution and extracted with 3×30 ml. of ether. The ether solution is washed with 10 ml. saturated sodium chloride solution and dried above magnesium sulphate. When the solvent is distilled off 1.063 g. of the named compound is obtained in the form of an oil, yield: 94.7%. $R_f$: 0.33, eluant: 1:1 mixture of hexane-acetone.

The obtained product is then treated with 2 ml. of acetanhydride for 14 hours in 5 ml. of pyridine and thus a triacetyl derivative identical with the product of Example 1 is obtained.

EXAMPLE 3

4-thia-β-PGI$_1$-methyl-ester (Compound of the formula I wherein Q=—S—, A=—CH$_2$—CH$_2$, Z=—COOCH$_3$, B=trans-vinylene, $R^1$ and $R^3$=hydrogen, $R^2$=n-pentyl)

0.601 g. (0.022 mole) of a compound obtained in Example 2 is dissolved in 20 ml. of anhydrous ethanol, 0.8 ml. of acrylic acid methyl ester is added to the solution and a few drops of a 5% ethanolic sodium ethylate solution is added to the reaction mixture under stirring. The reaction is completed at room temperature within 1–2 hours. The reaction can be followed on a silicagel thin layer with a 1:1 hexane-acetone mixture eluant. $R_f$ of the named compound: 0.33 and for the starting material: 0.27. When the reaction is completed ethanol is removed from the reaction mixture by rotating evaporator and the residue is chromatographed on a 100 g. of silicagel column and eluted with a 1:1 mixture of acetone-hexane. 0.678 g. (88%) of 4-thia-β-PGI$_1$ methyl ester is obtained.

$H^1$-NMR (CDCl$_3$): 5.5 (m, 2H), 4.43 (q, 1H), 4.16 (m, 1H), 4.06 (m, 1H), 3.66 (s, 3H), 3.61 (m, 1H), 2.84–2.85 (m, 7H), 2.5–1.15 (m, 15H), 0.84 (t, 3H) ppm.

EXAMPLE 4

3(R,S)-methyl-4-thia-β-PGI$_1$-methyl-ester (Compound of the formula I wherein Q, Z, B, $R^1$, $R^2$, $R^3$ are the same as in Example 3., and A=CH(CH$_3$)—CH$_2$—

One may proceed as in Example 3 but acrylic acid methyl ester is replaced by 0.8 ml. of crotonic acid methyl ester. The named compound is obtained with a yield of 66% in the form of an epimeric mixture which cannot be separated by chromatography. The components of the mixture differ from each other in the absolute steric configuration of the methyl substituent on the 3-carbon-atom.

$R_f$=0.31 eluted with an 1:1 mixture of hexane and acetone.

$H^1$-NMR(CDCl$_3$): 5.53 (m, 2H), 4.45 (q, 1H), 4.25–3.97 (M, 2H), 3.67 (s, 3H), 3.60 (m, 1H), 3.22 (m, 1H), 2.56–1.18 (m, 20H), 1.33 (2d, 3H, J=7.5 Hz), 0.87 (t, 3H) ppm.

EXAMPLE 5

4-Thia-β-PGI$_1$-nitrile (Compound of the formula I, wherein A, B, $R^1$, $R^2$, $R^3$, Q are as defined in Example 3, Z=C≡N)

One may proceed as disclosed in Example 3 but acrylic acid methyl ester is replaced by 0.8 ml. of acrylo nitrile. 0.629 g. (89%) of the named compound is obtained in the form of colorless oil. $R_f$=0.21 (eluent: 1:1 mixture of acetone-hexane).

IR (film): 3300–3100 (associated OH), 2190 (C≡N) cm$^{-1}$.

EXAMPLE 6

4-thia-β-PGI$_1$ (Compound of the formula I, wherein A, B, $R^1$, $R^2$, $R^3$ and Q are the same as given in Example 3, Z=COOH).

0.386 g. (0.001 mole) of 4-thia-β-PGI$_1$-methyl ester obtained in Example 3 is dissolved in 10 ml. of methanol and under stirring 2 ml. of 0.5 mole sodium hydroxide solution are added. The reaction mixture is allowed to stand at room temperature for 24 hours while the ester is completely saponified (on the layer chromatogram the $R_f=0.27$ spot corresponding to the ester disappears and a spot hardly moving from the starting point appears.) Methanol is evaporated by rotation in vacuo and the residue is acidified with 1 ml. of 1 M aqueous sodium hydrogen sulfate solution, extracted with 30 ml. of an 1:1 ether-ethyl acetate mixture, the organic solution is washed with 2×5 ml. of saturated sodium chloride solution and dried above magnesium sulphate. After removing the solvent the title compound remains as 0.360 g. (96.6%) of crystalline substance which can be recrystallized from an ether-hexane or an ethyl acetate-hexane mixture.

$R_f=0.18$ eluent: a 20:10:1 mixture of benzene-dioxaneacetic acid.

EXAMPLE 7

4-Sulfinyl-β-PGI$_1$-methyl ester (Compound of the general formula I wherein A, B, Z, R$^1$, R$^2$, R$^3$ are the same as in Example 3 and Q=—SO—)

1.00 g. (0.0026 mole) of 4-thia-PGI$_1$ methyl ester as prepared according to Example 3 is dissolved in 20 ml. of anhydrous dichloromethane, the solution is cooled to 0° C. and 0.55 g. (0.0032 mole) of 3-chloro-perbenzoic acid is added in 15 minutes under stirring in small portions. After further stirring for 30 minutes the solution is washed in a shaking funnel with 5 ml. saturated sodium hydrogen carbonate solution, 5 ml. 5% sodium hydrogen sulfate solution, and with 2×5 ml. water. The solvent is removed in vacuo after drying above magnesium sulphate. 0.845 g. of the crude named compound is obtained.

Yield: 81%.

$R_f=0.106$, eluted with an 1:2 mixture of acetone-hexane, on silicagel.

We claim:

1. A 4-thia- or 4-sulfinyl-PGI$_1$-compound of the formula I

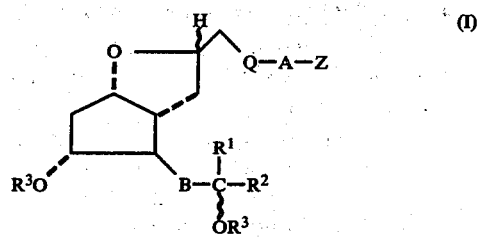

wherein
Q stands for —S— or —SO—,
A stands for C$_{1-6}$ straight or branched chain alkylene,
B stands for ethylene, vinylene or ethynylene,
R$^1$ represents hydrogen or C$_{1-4}$ alkyl,
R$^2$ represents C$_{1-8}$ straight or branched chain alkyl,
R$^3$ stands for hydrogen or acetyl, and
Z represents —COOH, —CN, —CH$_2$OH or —COOW, wherein W stands for an equivalent of a pharmacologically acceptable cation or C$_{1-4}$ alkyl.

2. 4-Thia-β-PGI$_1$-methyl ester as defined in claim 1.

3. 3-(R,S)-Methyl-4-thia-β-PGI$_1$-methyl ester as defined in claim 1.

4. 4-Thia-β-PGI$_1$-as defined in claim 1.

5. 4-Thia-β-PGI$_1$-nitrile as defined in claim 1.

6. 4-Sulfinyl-β-PGI$_1$-methyl ester as defined in claim 1.

7. Pharmaceutical compositions inhibiting aggregation, having vasodilative, bronchodilative and stomach mucosa protective activity comprising as active ingredient an effective amount of one or more compounds as defined in claim 1 and a diluent.

8. A platelet inhibiting, vasodilative, bronchodilative and stomach-mucosa-protective method of treatment which comprises administering to a subject in need thereof an effective amount of a compound as defined in claim 1.

* * * * *